(12) United States Patent
Weiler et al.

(10) Patent No.: US 7,924,502 B2
(45) Date of Patent: *Apr. 12, 2011

(54) MICROSCOPE WITH CENTERED ILLUMINATION

(75) Inventors: Andreas Weiler, Alstätten (CH); Haw Chong Soon, Widnau (CH)

(73) Assignee: Leica Instruments (Singapore) Pte. Ltd., Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 12/145,863

(22) Filed: Jun. 25, 2008

(65) Prior Publication Data

US 2009/0002814 A1 Jan. 1, 2009

(30) Foreign Application Priority Data

Jun. 28, 2007 (DE) .................... 10 2007 029 895

(51) Int. Cl.
G02B 21/06 (2006.01)
G02B 21/00 (2006.01)

(52) U.S. Cl. ...................................... 359/385; 359/368

(58) Field of Classification Search ........... 359/368–390
See application file for complete search history.

(56) References Cited

U.S. PATENT DOCUMENTS

| 4,674,845 | A | * | 6/1987 | Matsumura | 359/377 |
|---|---|---|---|---|---|
| 5,155,509 | A | * | 10/1992 | Kleinberg | 351/205 |
| 5,748,367 | A | * | 5/1998 | Lucke et al. | 359/385 |
| 5,838,491 | A | * | 11/1998 | Gartner et al. | 359/385 |
| 5,973,829 | A | * | 10/1999 | Moller et al. | 359/389 |
| 6,072,622 | A | * | 6/2000 | Biber | 359/368 |
| 6,392,797 | B2 | * | 5/2002 | Strahle | 359/389 |
| 6,473,229 | B2 | | 10/2002 | Nakamura | |
| 6,816,304 | B2 | * | 11/2004 | Nakamura et al. | 359/388 |
| 6,972,900 | B2 | * | 12/2005 | Sander | 359/372 |
| 7,102,818 | B2 | | 9/2006 | Sander | |
| 2001/0010592 | A1 | | 8/2001 | Nakamura | |
| 2003/0048530 | A1 | | 3/2003 | Sander | |
| 2003/0201378 | A1 | * | 10/2003 | Ishikawa et al. | 250/201.3 |
| 2004/0057108 | A1 | | 3/2004 | Namii | |
| 2004/0136059 | A1 | | 7/2004 | Sander | |
| 2009/0021827 | A1 | * | 1/2009 | Chong | 359/389 |

FOREIGN PATENT DOCUMENTS

DE 195 23 712 C2 1/1996

(Continued)

OTHER PUBLICATIONS

Office Action issued by the United States Patent and Trademark Office for U.S. Appl. No. 12/145,868 dated Jun. 8, 2009.

(Continued)

*Primary Examiner* — Thong Nguyen
(74) *Attorney, Agent, or Firm* — Schlee IP International, P.C.; Alexander R. Schlee

(57) ABSTRACT

A microscope comprising a main objective including a lens assembly movable in the direction of the optical axis of the main objective for focal length variation and comprising an illuminating unit with an illumination deflector element for generating an illuminating beam path directed onto an object plane and extending outside the main objective. The position of the illumination deflector element is adjustable dependent on a focal length variation of the main objective for centering the illumination. The illumination deflector element is movable in a direction parallel to the optical axis of the main objective and is coupled to the movable lens assembly of the main objective.

17 Claims, 2 Drawing Sheets

FOREIGN PATENT DOCUMENTS

| | | |
|---|---|---|
| DE | 195 37 868 B4 | 4/1996 |
| DE | 10144062 | 3/2003 |
| EP | 0321586 | 6/1989 |
| EP | 1 424 582 B1 | 6/2004 |
| EP | 1424582 | 6/2004 |

OTHER PUBLICATIONS

Office Action issued by the United States Patent and Trademark Office for U.S. Appl. No. 12/145,868 dated Mar. 31, 2010.

* cited by examiner

MICROSCOPE WITH CENTERED ILLUMINATION

This application claims the priority of the German patent application DE 10 2007 029 895.3 having a filing date of Jun. 28, 2007, the entire content of which is herewith incorporated by reference.

BACKGROUND OF THE INVENTION

The present invention relates to a microscope comprising a main objective having a lens assembly movable in the direction of the optical axis of the main objective for focal length variation and comprising an illuminating unit with an illumination deflector element for generating an illuminating beam path that is directed onto an object plane and extends outside the main objective, the position of the illumination deflector element being adjustable dependent on a focal length variation of the main objective for centering the illumination.

Microscopes of this type are known from DE 195 23 712 C2 and DE 195 37 868 B4. In the first-mentioned DE 195 23 712 C2 a stereomicroscope comprising a main objective with variable focal length, a downstream zoom system and a binocular tube as well as an illuminating unit arranged adjacent to the main objective is disclosed. The main objective comprises a fixed and a movable lens for varying the focal length and the intercept length of the main objective. The fixed, negative lens of the main objective is arranged towards the object plane, the movable, positive lens is arranged behind it (facing away from the object plane). A movement of the movable lens in the direction away from the object plane results in a reduction of the focal length of the main objective. For an optimal illumination of the vertically shifting object plane, it is suggested in this document to adjust the position of an illumination deflector element dependent on a focal length variation of the main objective for centering the illumination. This is done in that the prism lens used as an illumination deflector element is pivoted such that the illuminating beam path tracks the changed object plane. For this purpose, the prism lens is pivotally mounted about an axis which is perpendicular to a plane that is spanned by the vertical optical axis of the main objective and the illuminating beam path which is incident substantially horizontally inclined on the prism lens. As a result thereof, for all positions of the movable lens of the main objective facing away from the object a focusing of the illuminating light on the respective focal point of the main objective can be guaranteed.

The coupling of the rotary movement of the illumination deflector element with the linear (vertical) movement of the lens of the main objective facing away from the object, as suggested in this document, requires very sensitive rotary movements of the illumination deflector element in relation to the movement of the lens and makes high demands on the mechanical coupling which is designed with a high constructional expense in this document. Any disturbances will be directly visible for the user (particularly given high magnifications). Further, the size of the surface of the deflector element turns out to be disadvantageous, as it has to be sufficiently large in order to cover the entire illuminating pencil even when the illumination deflector element is tilted. Mirrors or the mentioned prism lenses can be used as illumination deflector elements. When mirrors are used, an enlargement of the reflecting surface will result in the additional disadvantage of an increased required thickness of the reflecting surface. Thus, altogether the required space and the height of the weight to be moved are increased.

In the mentioned DE 195 37 868 B4, an illuminating device for a stereomicroscope comprising an objective with a variable image-forming intercept length is disclosed, an illumination intercept length variation being possible via an optical system that is separate from the viewing optical system. Means for coupling the intercept lengths mentioned are disclosed, which means effect that the illumination intercept length and the image-forming intercept length correspond to one another. Further, means for coupling are provided which guarantee that the angular position of a deflector element of the illuminating device is varied such dependent on the respective image-forming intercept length and illumination intercept length that there is always a centered illumination of the viewed field of view. Since, for centering the illumination, here too, rotary movements of the illumination deflector element are performed, here, once again the disadvantages mentioned occur.

A basically different possibility of illumination centering results when the illumination is guided through the main objective of the microscope. This solution is implemented in the surgical microscope models M520 and M525 of the applicant. Here, the illumination deflector element directs the illuminating beam path to and through the main objective having a variable focal length so that the illumination is always centered on the focus.

The microscopes mentioned up to now use vertical zoom systems, i.e. the longitudinal axis of the zoom system lies parallel to the optical axis of the main objective. If, in addition, the illumination is fed into the main objective from above, there will be a high space requirement in vertical direction resulting in microscopes having a relative high overall height in the vertical direction. This is in turn disadvantageous for ergonomic reasons since the distance between the eyepiece and the main objective is increased.

For solving the last-mentioned problem, a stereomicroscope structure has been suggested in the document EP 1 424 582 B1, in which a "lying" zoom system, i.e. a zoom system having its longitudinal axis arranged horizontally, is realized. For this purpose, there is arranged between the main objective and the zoom system a deflector element which deflects the viewing beam path from a substantially vertical direction into a substantially horizontal direction and feeds the same into the zoom system arranged in a first horizontal plane. By means of further deflector elements the viewing beam path exiting the zoom system is deflected into a second horizontal plane which extends substantially parallel to the first horizontal plane and in which optical add-on components are arranged. With respect to details on the structure and the mode of functioning of such a stereomicroscope with "lying" zoom system reference is explicitly made to the mentioned European patent specification.

In this stereomicroscope, the illuminating unit is arranged substantially adjacent to the main objective und below the zoom system, the illuminating beam path being guided outside the main objective. Instead of an illumination centering, it can be ensured by means of a sufficiently large illuminated field that the visual field is always illuminated given a focal length variation of the main objective. Such a generously designed illuminated field requires a correspondingly largely designed illuminating aperture and thus illuminating unit, which in turn has a negative effect on the ergonomics of the microscope. A further disadvantage in this connection is that the homogeneity of the illumination (intensity in the illuminated field) cannot be the same for all positions of the multifocus (variable focus lens). Only another section of the entire available illuminated field is used.

The present invention shall be particularly suitable for illumination centering in a microscope structure making use of "lying" zoom systems.

SUMMARY OF THE INVENTION

The problem to be solved by the present invention is to realize in a technically easy way a centering of the illumination given a focal length variation of the main objective of the microscope.

The inventive microscope comprises a main objective having a variable focal length, for which a lens assembly movable in the direction of the optical axis of the main objective is provided. In this application, the terms multi-focus or variable focus lens shall refer to such a main objective of variable focal length. Without restricting the generality, it is assumed in the following that this main objective comprises a fixed part, facing away from the object, and a movable, object-facing part, each of these parts including a lens assembly. A lens assembly can comprise a single lens or a combination of lenses. The variable focus lens can, for example, be constructed such that the lower, object-facing part is fixed, and the upper part, facing away from the object, is movably designed. By using such a variable focus lens different object planes can be focused in a certain area.

DETAILED DESCRIPTION OF THE INVENTION

The inventive microscope further comprises an illuminating unit with an illumination deflector element for generating an illuminating beam path that is directed onto an object plane and extends outside the main objective, wherein it shall be assumed, without restricting the generality, that the illuminating beam path generated by the illuminating unit is incident on the illumination deflector element in a direction which is substantially perpendicular (or inclined) to the optical axis of the main objective. The illumination deflector element directs this illuminating beam path in the direction of the object plane onto the focus of the main objective. The optical axis of the main objective is in this case perpendicular to the object plane.

According to the invention, the illumination deflector element is movably arranged parallel to the optical axis of the main objective and coupled to the movable lens assembly of the main objective. Thus, the linear (vertical) movement of the movable lens assembly of the variable focus lens is coupled with a linear (vertical) movement of the illumination deflector element, which movement is parallel thereto. Such a coupling is technically easier to realize than the known coupling of a rotary or tilting movement of the illumination deflector element with the linear movement of the lens assembly in the variable focus lens.

In principle, two different possibilities for varying the focal length of a main objective can be distinguished which shall be explained in more detail in the following. Of course, many different structures of variable focus lenses or multi-focus lenses are known, the person skilled in the art usually being able to readily apply the present invention onto the respective specific structure of the variable focus lens. This shall be illustrated on the basis of the two basic possibilities mentioned:

The variable focus lens (multi-focus lens) can be composed of two lens assemblies having focal lengths with different signs, which lens assemblies are mounted such that they can be moved relative to one another. Given this structure, an increase in the distance between the two lens assemblies results in a reduction of the working distance, the focal length and the intercept length of the main objective.

As a second possibility, two lens assemblies having focal lengths with positive signs can be used in a variable focus lens (multi-focus lens), which lens assemblies are movably mounted relative to one another. In this case, an increase in the distance between the two lens assemblies results in an increase in the working distance, the focal length and the intercept length of the main objective.

The coupling of the two mentioned linear movements can take place in the same sense or in the opposite sense, dependent on the mode of functioning of the variation of the focal length by means of the linear movement of the lens assembly. The coupling can have the ratio 1:1, but also other ratios. For example, given a reduction in working distance and the corresponding reduction of the field of view an illuminated field could be desired which is greater in relation to the field of view in order to illuminate, for example, a larger area of a surgical field. As additional parameters, diaphragms and/or lens systems in the illuminating system can still be varied with an optical effect in order to achieve the desired illumination centering. This will still be explained in more detail further below. In a preferred embodiment, it is, for example, in particular possible to connect the illumination deflector element firmly to the movable lens assembly of the main objective. Thus, the illumination centering is directly (inevitably) tracked to a variation in focal length.

Of course, it has to be taken into account that the illuminating beam path generated by the illuminating unit is incident on the illumination deflector element coupled or firmly connected to the movable lens assembly over the entire shifting range of this lens assembly of the main objective. For this purpose, there would be, at first, the basically conceivable possibility to design the diameter of the illuminating beam path incident on the illumination deflector element sufficiently large such that over the entire moving range of the illumination deflector element sufficient light is incident thereon.

Another possibility is that at least a part of the illuminating unit is designed such that the illuminating beam path generated by the illuminating unit follows a movement of the illumination deflector element. This can be effected, for example, by a mechanical coupling or via electronically drivable deflector elements in the illuminating unit. However, a mechanical solution is likewise possible in which at least a part of the illuminating unit is designed such that it is movable in parallel to the direction of movement of the illumination deflector element. In other words, then at least a part of the illuminating unit moves parallel (in vertical direction) to the illumination deflector element which in turn is coupled or firmly connected to the movable lens assembly.

In another, particularly preferred embodiment at least a part of the illuminating unit is tiltably mounted about an axis which is substantially perpendicular to a plane spanned by the optical axis of the main objective and the axis of the illuminating beam path. By tilting the illuminating unit or at least a suitable part thereof, the illuminating beam path can thus each time be tracked or guided in the direction of the position of the illumination deflecting mirror.

It is expedient to provide a control electronics which controls the coupling of the movement of the illumination deflector element with the illuminating beam path generated by the illuminating unit. In particular, this control electronics controls a required movement of at least a part of the illuminating unit according to the just explained embodiments dependent on the movement of the movable lens assembly of the main objective.

Suitable illuminating units to be used in the present microscopes are known per se. Light can be supplied to the illuminating unit via a light guide. For example halogen, xenon or LED lamps can likewise be used. Without restricting the generality, a structure is assumed in which the supplied light is collected by a collector and focused via a diaphragm and a downstream lens system on the object plane. The lens system can be composed of a fixed and a movable lens, the movable lens being movable in axial direction relative to the fixed lens. As a result thereof, the illumination intercept length can be varied.

With respect to the above-mentioned embodiment of an illuminating unit which is at least partially tiltable about an axis, it is useful with respect to the mentioned structure of the same to not design the entire illuminating unit tiltably but only a part thereof which is substantially formed by the mentioned diaphragm and the mentioned lens system. This part can easily be separated from the collector and the light source.

If the already mentioned diaphragm is present in the illuminating unit for adjusting an illuminated field diameter, it is advantageous to vary the opening diameter of the diaphragm dependent on a movement of the movable lens assembly of the main objective. As a result thereof, the illuminated field diameter, i.e. the illuminated part in the object plane, can be directly influenced. For example, given an increasing working distance, the field of view increases so that by means of a corresponding increase in the diaphragm opening the size of the illuminated field can be adapted to the increased field of view. Correspondingly, given a decreasing working distance the diaphragm opening can be decreased, unless in a specific case, a greater illuminated field is desired.

Here, again, it is useful, to control by means of a control electronics the opening diameter of the diaphragm dependent on a movement of the movable lens assembly of the main objective. This control electronics can be one that cooperates with the already mentioned control electronics for the control of the coupling of a movement of the illumination deflector element with the illuminating beam path generated by the illuminating unit or one that is integrated thereinto.

Given the presence of the already mentioned lens assembly in the illuminating unit having a lens axially movable relative to a fixed lens, it is advantageous when the position of the movable lens can be varied dependent on a movement of the movable lens assembly of the main objective. As a result thereof, in addition to the inventive centering of the illumination, the illumination intercept length can likewise be adapted to the image-forming intercept length of the main objective. Again, a control electronics for controlling said procedure is useful, wherein this control electronics can again be combined with the already mentioned control electronics or can be integrated into them.

The illumination deflector element of the illuminating unit of the microscope according to the invention can be an illumination deflector element having a plane or a spherical reflecting surface. A spherical reflecting surface has, in addition to the lens group present in the illuminating unit, a focusing effect which can be advantageously used.

For constructional, optical and ergonomic reasons the use of the present invention is particularly suitable in a microscope having a "lying" zoom system (see the explanations made at the beginning). For this purpose, a zoom system is arranged downstream of the main objective, as viewed from the object plane, a deflector element being arranged between the zoom system and the main objective, which element deflects the viewing beam path coming from the main objective into a first horizontal plane in which the longitudinal axis of the zoom system lies. Below the zoom system, i.e. on its object-sided side, the illuminating unit of the microscope can then be arranged axially parallel. As a result thereof, one obtains a structure having a relative low overall height in vertical direction. Usually, the microscope has a tube and at least one eyepiece, in the case of a stereomicroscope a binocular tube, which are or, respectively, is arranged downstream of the zoom system. However, it shall also be noted here that between the magnification changer (zoom system) and the tube an output (optical and mechanical) can be present for documentation, to which output, for example, a camera can be connected. Via optical deflector elements, the viewing beam path reaches from the mentioned first horizontal plane into a second horizontal plane which extends parallel thereto and in which optical add-on components and/or the tube are arranged. By means of this folding of the viewing beam path a microscope structure having a low overall height is guaranteed and in addition manifold possibilities of a coupling-out, for example, given a surgical microscope for assistant's viewing are created.

The present invention and its advantages shall be explained in more detail in the following on the basis of an embodiment illustrated in the enclosed drawing.

DETAILED DESCRIPTION OF THE DRAWINGS

Figure 1:
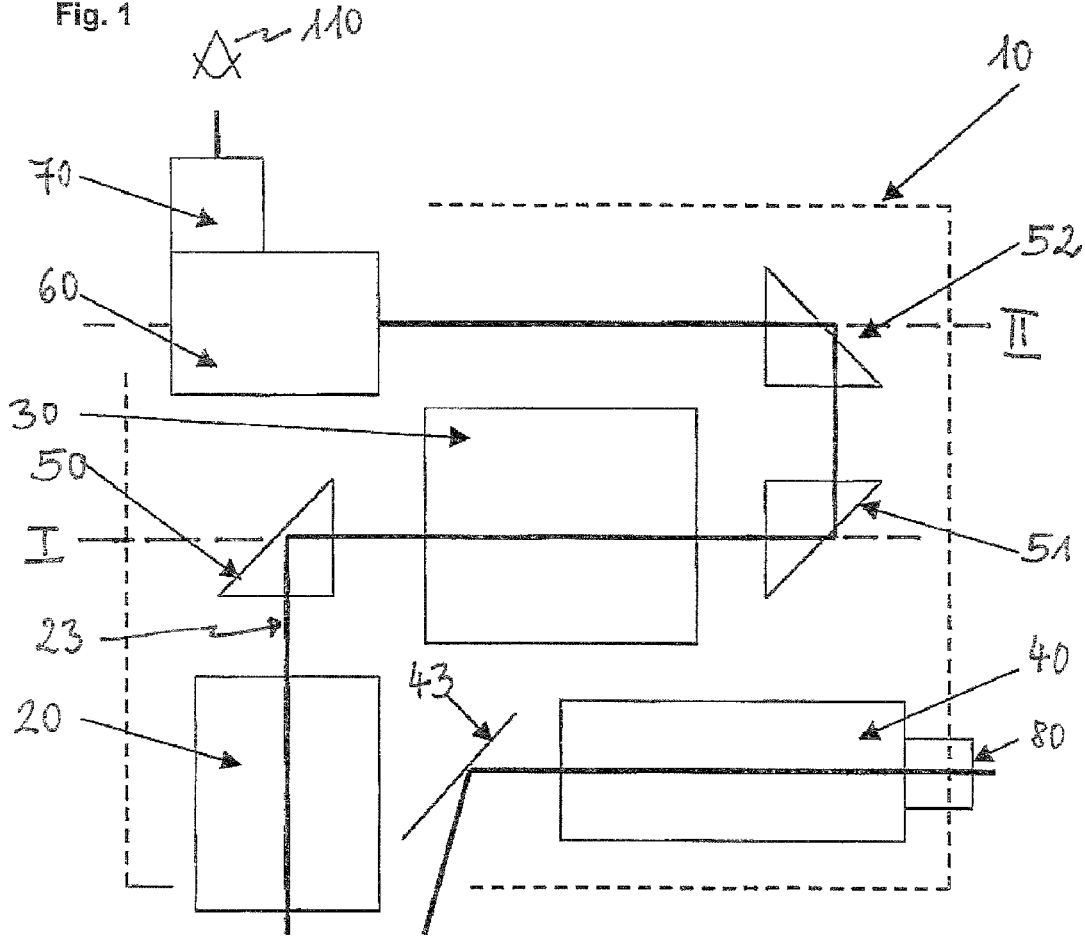
FIG. 1 schematically shows the structure of a microscope with which the invention can preferably be used.

FIG. 1 schematically shows the basic structure of a microscope 10, here designed as a surgical stereomicroscope, for a better illustration only the viewing axis being illustrated instead of the two viewing beam paths. Such surgical microscopes often have an additional pair of viewing beam paths for assistant's viewing. Microscopes of this type are known per se and therefore shall not be explained in more detail here. In this connection, reference is made to the stereomicroscope described in the already mentioned EP 1 424 582 B1 in which, as in the present case, a "lying" zoom system 30 is realized.

The surgical microscope 10 comprises a main objective 20 which is designed as a multi-focus (or variable focus lens), i.e. represents a lens having a variable focal length. The main objective 20 defines an optical axis 23 which is perpendicular to an object plane 100. By varying the focal length of the main objective 20, focusing on the respective object plane 100 can be effected. The viewing beam paths extend parallel to the shown optical axis 23 and lie, for example, either in the drawing plane or in a plane perpendicular to the drawing plane and including the optical axis 23. For deflecting the viewing beam paths a first deflector element 50 is arranged in the beam path and deflects the viewing beam paths from a substantially vertical direction into a substantially horizontal direction into the "lying" zoom system 30. The zoom system 30 is arranged with its longitudinal axis in a first horizontal plane I. Instead of a zoom system 30 which serves for the continuous magnification of the object image a discretely operating magnification changer can likewise be provided. By means of further deflector elements 51 and 52, the viewing beam path is directed into a second horizontal plane II. Here, the tube 60 is arranged, which directs the viewing beam path into an eyepiece 70 through which an observer 110 can view the microscope image. The principle structure of the described microscope components such as main objective, zoom system, tube and eyepiece is common knowledge for the person skilled in the art. In the beam path illustrated in FIG. 1, optical add-on components such as filters, image inverters, components for extending the optical path length, optical beam splitters for assistant's viewing, etc. can be arranged. Finally, between the zoom system 30 and the actual tube 60 an output (optical/mechanical) for documentation (camera, video, etc.) can be present.

An illuminating unit 40 which can be arranged ergonomically favorable with its longitudinal axis substantially horizontally below the zoom system 30 serves for the illumination of the object. What is illustrated here is a fiber illumination via an optical light guide 80. However, a direct halogen, xenon or LED illumination can likewise be used. The illuminating beam path generated by the illuminating unit 40 and illustrated by means of its illuminating axis is directed by means of an illumination deflecting mirror 43 in the direction of the object plane 100. As can be taken from FIG. 1, the illuminating beam path is guided outside the main objective 20 of the microscope 10. Consequently, given a variation in focal length of the main objective 20 which results in a shift of the object plane 100 in vertical direction, the illuminating beam path has to be tracked (re-adjusted) for an optimal illumination. The inventive type of this tracking of the illumination shall be explained in more detail on the basis of FIG. 2.

Figure 2:
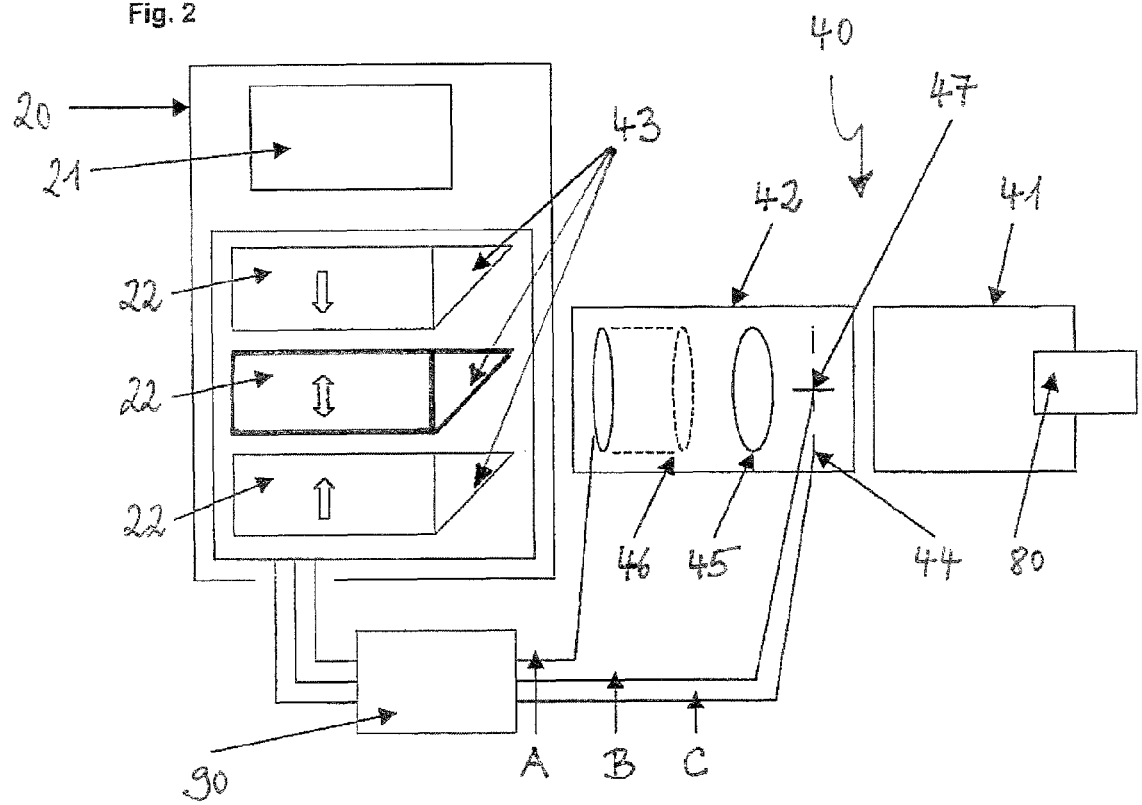
FIG. 2 schematically shows a cutout of the microscope according to FIG. 1, which shows the essential components of the invention.
Figure 2:

FIG. 2 schematically shows a cutout of a microscope 10 from FIG. 1, which cutout is limited to the schematic illustration of the main objective 20 and the illuminating unit 40.

The main objective 20 is basically composed of two parts which can be moved relative to one another along the optical axis 23 for varying the focal length of the main objective 20. Without restricting the generality, it is assumed in the following that for this purpose an upper fixed lens assembly 21 as well as a lower movable lens assembly 22 are provided. Other possibilities for realizing a variable focus lens are known to the person skilled in the art, for example, also an inverted structure in which the lower part is fixed and the upper part is axially movable.

The illuminating unit 40 comprises, in this specific example, the already described light guide 80 and a collector 41 which collects the light coming from the light guide 80 and images the same via the lens assembly 45, 46 into the object plane 100. A diaphragm, for example, an iris diaphragm 44 having an adjustable opening diameter serves for the direct control of the illuminated field diameter, i.e. the illuminated part in the object plane 100. The illuminating unit 40 can comprise an illuminating optical system for varying the illumination intercept length. This illuminating optical system is here illustrated on the basis of two lenses 45 and 46, the lens 45 being fixed and the lens 46 being designed axially movably. By means of such an illuminating optical system the illumination intercept length can be adapted to the respective viewing intercept length of the main objective 20. The illuminating unit 40 can realize a Köhler illumination or another illuminating optical system. The structure described herein is merely exemplary. The invention can likewise be realized with illuminating units structured differently as well as other illuminating optical systems.

The illuminating unit 40 comprises an illumination deflector element 43 which is, according to the invention, movably arranged parallel to the optical axis 23 of the main objective 20 and is coupled to the movable lens assembly 22 of the main objective 20. In FIG. 2, altogether three different positions of the movable lens assembly 22 are illustrated. These positions are referred to in the following with "top", "intermediate" and "bottom". By movement of the movable lens assembly 22 from the bottom to the top, the focal length of the main objective 20 is varied. Accordingly, the illuminating focus has to be tracked to the varying focus planes of the main objective 20 in order to maintain an optimal illumination. For this purpose, the illumination deflector element 43 is, in this example, fixedly connected to the movable part, here the movable lens assembly 22 of the main objective 20. The illumination deflector element 43 is thus inevitably guided by the movable lens assembly 22. As an illumination deflector element a plane, but also a spherical reflecting surface can be used. This reflecting surface deflects the light of the illuminating unit 40 downwardly into the object plane 100 to be illuminated, so that the illumination centering on which the invention is based is guaranteed.

In order to make sure that there is sufficient light incident on the illumination deflector element 43 and thus on the object plane 100 over the entire moving range of the lens assembly 22 of the main objective 20, it is useful to track the illuminating beam path to the movement of the deflector element 43. For this purpose, in preferred embodiments either the entire illuminating unit 40 is tracked to the movement of the illumination deflector element 43 in vertical direction or the illuminating unit 40 is designed at least partially tiltably or rotatably, as will be explained in the following. In FIG. 2, the illuminating unit 40 is illustrated in the two-part form. The rear part (as seen in the direction of the illuminating beam path) substantially is comprised of the light guide 80 and the collector 41. Separated therefrom, is the front part which is substantially comprised of the illustrated and already explained components of an iris diaphragm 44 and an illuminating optical system including the fixed lens 45 and the movable lens 46. The front tiltable (rotatable) part 42 of the illuminating unit 40 is mounted about a rotary point or about a rotary axis 47 which is perpendicular to the drawing plane and lies in the center of the iris diaphragm 44. By tilting the front part 42 of the illuminating unit 40 about the rotary axis 47, the linear movement of the illumination deflector element 43 can thus be followed. In the embodiment illustrated here, the horizontal position of the front part 42 of the illuminating unit 40 coincides with the position "intermediate" of the illumination deflector element 43 or, respectively, the movable lens assembly 22 of the main objective 20. It can be useful to assign said horizontal position of the front part 42 of the illuminating unit 40 to the position "bottom" or an arbitrary other position of the movable lens assembly 22. The embodiment of the tiltable illuminating unit is particularly preferred for an optimal illumination centering.

In FIG. 2, there is further illustrated a control electronics 90 which can be a standard control unit in the general sense. This control electronics 90 couples the movement of the front part 42 of the illuminating unit 40 about the rotary axis 47 with the movement of the movable lens assembly 22 of the main objective 20 (coupling B). In this way, there can be a synchronous tracking of the illuminating beam path.

It is advantageous when further couplings are established in the inventive microscope structure. Expediently, these couplings are likewise taken over by the control electronics 90.

On the one hand, the adjustable opening diameter of the iris diaphragm 44 can be coupled with the linear movement of the movable lens assembly 22 of the main objective 20 (coupling C). For this purpose, given a movement from the position "bottom" in the direction of the position "top", which can, for example, result in an increase in the illumination intercept length and the focal length of the main objective, the illuminated field diameter is increased, i.e. the iris diaphragm 44 is further opened. In this way, the illuminated field can be adapted to the varying field of view.

On the other hand, the axial movement of the movable lens 46 of the illuminating unit 40 can be coupled with the linear movement of the movable lens assembly 22 of the main objective 20 (coupling A). In this way, the varied intercept length of the main objective 20 can be taken into account by means of a corresponding variation of the illumination intercept length. As a result thereof, in turn the intensity in the illuminated field can be varied or adapted.

By means of the mentioned couplings A to C, given a variation of the focal length of the main objective 20, the illuminating focus can be tracked in a centered way, the illuminated field diameter can be adapted to the diameter of the field of view and the illuminated field intensity can be adjusted.

The mentioned couplings A, B and C can be electronically implemented. For this purpose, motor combinations, comprising a transmission, a motor and an encoder, are used. For path measurement (shifting of the shiftable components) sensors can be used (for example, displacement sensors). All required signals and commands are correspondingly processed and implemented in the control electronics 90. It is noted that the mentioned couplings A, B and C can also be realized mechanically.

The features of the invention described in the present specification cannot only be realized in the combination as illustrated herein, but also, as far as useful, alone or in other combinations without leaving the scope of the invention.

LIST OF REFERENCE NUMERALS 10 microscope
20 main objective
21 fixed lens assembly
22 movable lens assembly
23 optical axis
30 zoom system
40 illuminating unit
41 collector
42 front part of the illuminating unit
43 illumination deflector means
44 diaphragm, iris diaphragm
45 fixed lens
46 movable lens
47 rotary axis
50 deflector element
51 deflector element
52 deflector element
60 tube
70 eyepiece
80 light guide
90 control electronics
100 object plane
110 observer
I first horizontal plane
II second horizontal plane

The invention claimed is:

1. A microscope comprising:
a main objective including a movable lens assembly, and
an illuminating unit with an illumination deflector element for generating an illumination extending along an illuminating beam path directed onto an object plane and extending outside the main objective, wherein
the movable lens assembly is movable along an optical axis of the main objective for setting various focal lengths of the main objective,
the position of the illumination deflector element is adjustable for centering the illumination dependent on various focal lengths of the main objective,
the illumination deflector element is arranged such that it is movable in parallel to the optical axis of the main objective, and
the illumination deflector element is directly firmly and fixedly connected to the movable lens assembly of the main objective such that it is inevitably guided by the movable lens assembly and keeps the illumination beam path centered onto the object plane regardless of the position of the movable lens assembly.

2. The microscope according to claim 1, wherein at least one part of the illuminating unit is designed such that the illuminating beam path generated by the illuminating unit tracks a movement of the illumination deflector element.

3. The microscope according to claim 2, wherein at least a part of the illuminating unit is movable in a direction parallel to the direction of movement of the illumination deflector element.

4. The microscope according to claim 2, wherein the at least one part of the illuminating unit is mounted in such a manner that it is tiltable around an axis that is substantially perpendicular to a plane extending between the optical axis of the main objective and the illuminating beam path.

5. The microscope according to claim 2, wherein a control electronics is provided for controlling the coupling of a movement of the illumination deflector element with the illumination beam path generated by the illuminating unit.

6. The microscope according to claim 1, wherein the illuminating unit comprises a diaphragm for adjusting an illuminated field diameter, the opening diameter of the diaphragm being variable dependent on a movement of the movable lens assembly of the main objective.

7. The microscope according to claim 6, wherein a control electronics is provided for controlling the opening diameter of the diaphragm dependent on a movement of the movable lens assembly of the main objective.

8. The microscope according to claim 1, wherein the illuminating unit comprises a lens movable along the axis of the illuminating beam path for varying the illumination intercept length, the position of the lens being variable dependent on a movement of the movable lens assembly of the main objective.

9. The microscope according to claim 8, wherein a control electronics is provided for controlling the position of the lens dependent on a movement of the movable lens assembly of the main objective.

10. The microscope according to claim 1, wherein the illumination deflector element has a planar reflecting surface.

11. The microscope according to claim 1, wherein the illumination deflector element has a spherical reflecting surface.

12. The microscope according to claims 1, wherein the microscope comprises a zoom system arranged downstream of the main objective as viewed from the object plane.

13. The microscope according to claim 12, wherein a deflector element is arranged between the zoom system and the main objective, said deflector element directing the viewing beam path coming from the main objective into a first horizontal plane in which the longitudinal axis of the zoom system lies.

14. The microscope according to claim 12, wherein the microscope comprises a tube and an eyepiece, both being arranged downstream of the zoom system.

15. The microscope according to claim 14, wherein at least the tube is arranged with its longitudinal axis in a second horizontal plane that extends substantially parallel to the first horizontal plane.

16. The microscope according to claim 1, wherein the microscope is designed as a stereomicroscope.

17. The microscope according to claim 16, wherein the microscope is designed as a surgical microscope.

* * * * *